United States Patent [19]

Bradford

[11] Patent Number: Plant 5,456

[45] Date of Patent: Apr. 30, 1985

[54] NECTARINE TREE (SUN DIAMOND)

[76] Inventor: Norman G. Bradford, 11875 E. Savana Rd., Le Grand, Calif. 95333

[21] Appl. No.: 535,265

[22] Filed: Sep. 23, 1983

[51] Int. Cl.[3] ..... A01H 5/03
[52] U.S. Cl. ..... Plt./41
[58] Field of Search ..... Plt./41

*Primary Examiner*—Robert E. Bagwill

[57] ABSTRACT

The present invention relates to a nectarine tree and more particularly to a new and distinct variety broadly characterized by a medium size, vigorous, hardy, productive and regular bearing tree, the fruit of which ripens in late June under the ecological conditions described, with the first picking on June 25, 1983. The fruit is freestone, has a full red skin color at shipping ripeness, good firmness, attractive shape, and a waxlike appearance.

1 Drawing Figure

BACKGROUND OF THE VARIETY

The instant variety most nearly resembles the Spring Red nectarine (U.S. Plant Pat. No. 3,619) but is distinguished therefrom by ripening seven days before Spring Red and an improvement thereon by having a full red color at shipping ripeness, a more attractively uniform and symmetrical shape, and a waxlike appearance. It is further distinguished by yellow flesh to the pit at shipping ripeness which turns slightly red at the pit when fully ripe.

The instant variety was propagated by me at Bradford Farms in Merced County (San Joaquin Valley), Calif., as the result of open pollination of a second generation seedling from a Red Diamond nectarine seed parent (U.S. Plant Pat. No. 3,165) crossed by an Autumn Free pollen parent (U.S. Plant Pat. No. 2,976). I asexually reproduced the resulting plant by budding and grafting, and such reproduction of plant and fruit characteristics were true to the original plant in all respects.

DRAWING

The accompanying photograph shows the characteristics of the whole fruit in skin color and form, a characteristic fruit divided on its suture plane showing the flesh and stone cavity, and a characteristic stone and leaves.

POMOLOGICAL CHARACTERISTICS

Referring now more specifically to the pomological characteristics of this new and distinct variety of nectarine tree, the following has ben observed under the ecological conditions prevailing near Le Grand, Merced County (San Joaquin Valley), Calif., and was developed at the stage of eating ripe in the 1983 growing season. All color plate identifications are by reference to Dictionary of Color, 1950 (2d ed) by Maerz and Paul.

TREE

General: Hardy, vigorous and dense, of medium size; spreading and vase shape, with desired shape and density determined by pruning. Very productive and regular bearing.

TRUNK

General: Medium diameter, brown, shaggy bark; numerous tan lenticles, $\frac{1}{4}''$ to $\frac{3}{8}''$ in length.

BRANCHES

Medium size, medium smooth surface; second year and older growth is brown in color, newer growth brown with some green on ventral side, brown on dorsal side. Numerous small, tan lenticles, $\frac{1}{8}''$ to 1/16″ in length.

LEAVES

Size: Medium — length, $4\frac{1}{2}''$, width, $1\frac{1}{4}''$. Medium thickness, smooth.

Form: Lanceolate. Base, broadly acute; apex, acutely pointed.

Margin: Finely serrated.

Veins: Pinnately net veined.

Petiole: Medium — average length, $\frac{3}{8}''$, medium thickness. Light green color.

Glands: Averaging two opposite, small, reniform, green glands on the petiole and base of leaf.

Stipules: Two per leaf, 3/16″ in length.

Color: Dorsal side dark green (24-J-1), ventral side Lincoln Green (23-J-4).

FLOWERS

Buds: Hardy, medium size, plumply obtuse, free.

Flowers: Medium season blooming compared with other varieties. Large, pink in color.

FRUIT

Maturity when described: Eating ripe, June 29, 1983.

Size: Uniform, medium size; axial diameter, $2\frac{5}{8}''$, transverse in suture plane, $2\frac{1}{4}''$.

Form: Uniform, symmetrical. Globose to slightly oblong. Longitudinal section elliptical, slightly oblong; transverse through diameter, round.

Suture: An inconspicuous or very shallow line extending from base to beyond apex, becoming very inconspicuous on dorsal side, and even more so as fruit ripens. Little or no depression beyond pistil point.

Ventral surface: Slightly rounded, lipped very slightly on both sides with somewhat equal lips.

Cavity: Generally rounded but elongated in the suture plane with suture showing on both sides. Cavity depth, $\frac{3}{8}''$, breadth, $\frac{3}{8}''$. A few minor branch marks on largest fruit.

Base: Truncate.

Apex: Short, rounded.

Pistil point: Very small, mostly oblique, a few apical.

Stem: Medium size. Length, $\frac{1}{4}''$, width, $\frac{1}{8}''$.

Skin: General — medium thickness, medium tender. Tenacious to flesh. Tendency to crack is slight.

Skin color: Solid red (Red Banana 5-L-9) with waxed appearance. Minute flecking near apex when mature. Waxed appearance.

Flesh:

*Amygdalin.*—Scarce, juice moderate.

*Texture.*—Firm, crisp.

*Fibres.*—Few, fine.

*Ripens.*—Evenly.

*Flavor.*—Subacid.

*Aroma.*—Wanting.

*Eating quality.*—Good.

Flesh color: Yellow (Corn 10-J-5) to the pit with slight reddish tinge in riper fruits. Surface of pit cavity, yellow (Ta Ming 10-L-6), with yellow fibres.

STONE

Freestone.

Form: Generally oval — elongated in the suture plane.

Hilum: Narrow.

Apex: Acute, equal sides, slightly flattened.

Surface: Irregularly furrowed near apex, ridged from base to above mid-point.

Ridges: Jagged toward base.

Color: Cinnamon (12-E-7).

Thickness of pit wall: $\frac{1}{4}''$.

Tendency to split: Slight.

Kernel: Oval form, sweet, viable. Width, 9/16", length, $\frac{3}{4}''$, thickness, 5/16". Pellicle is light yellow when first split.

USE

Market, good shipping and eating quality.

RESISTANCE TO INSECTS AND DISEASE

Good resistance to insects, medium resistance to disease.

The nectarine tree and its fruit herein described may vary in slight detail due to climatic and soil conditions under which the variety may be grown.

I claim:

1. A new and distinct variety of freestone nectarine tree, substantially as illustrated and described, which most closely resembles Spring Red (U.S. Plant Pat. No. 3,619) but is distinguished therefrom and an improvement thereon by having fruit which ripens about seven days earlier and at shipping ripeness has a better firmness, a waxlike appearance of the skin, and a very symmetrical and attractive shape.

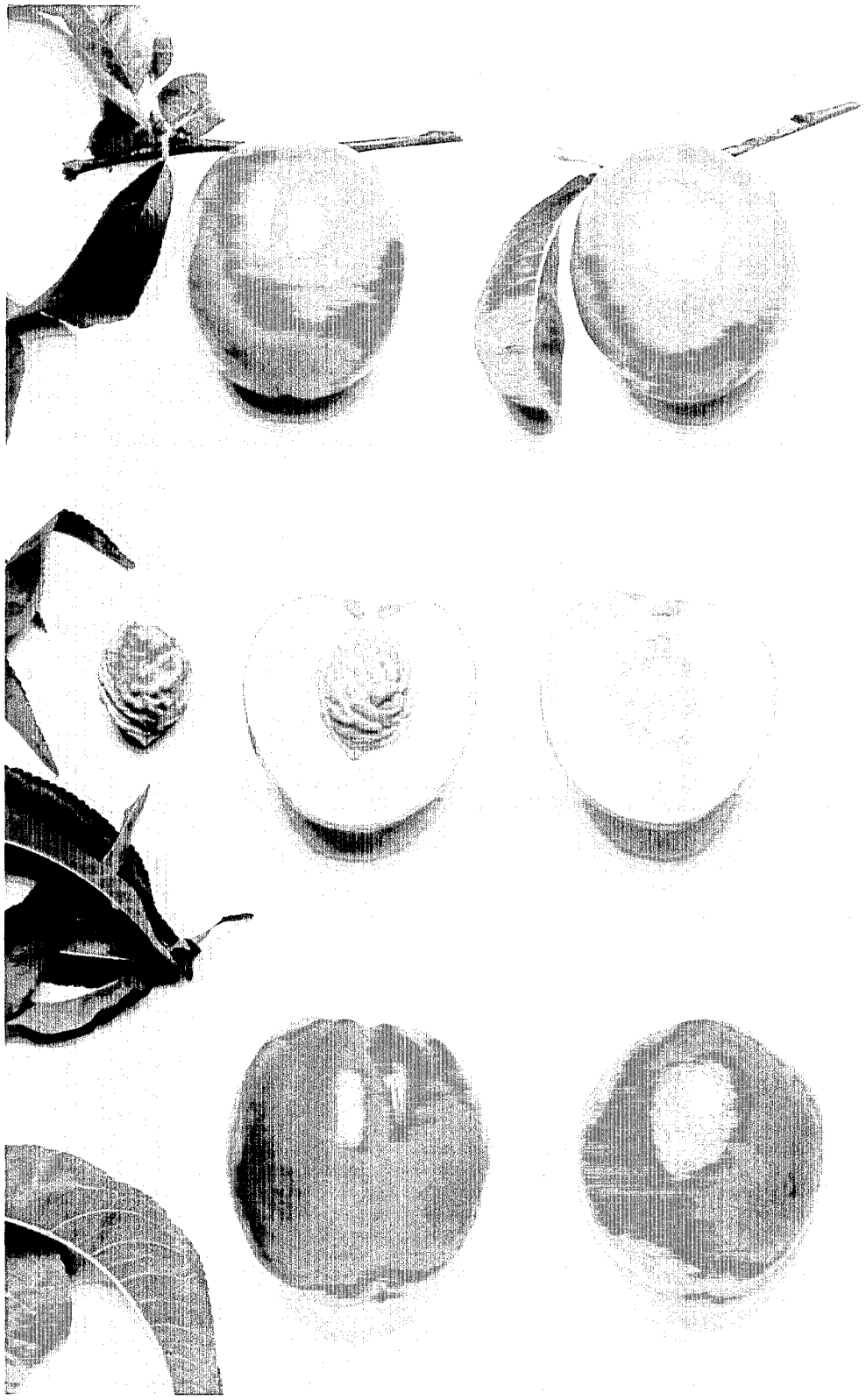

* * * * *